United States Patent
Tajiri et al.

(10) Patent No.: US 7,153,693 B2
(45) Date of Patent: Dec. 26, 2006

(54) METHOD AND APPARATUS FOR DETERMINING UREA CONCENTRATION

(75) Inventors: Yoshihiro Tajiri, Osaka (JP); Takuya Hayabuchi, Osaka (JP); Naohiro Teramoto, Osaka (JP); Yasuhiko Kojima, Chiba (JP); Eiji Sakata, Chiba (JP); Haruyuki Morikawa, Chiba (JP)

(73) Assignee: Toyo Engineering Corporation, Tokyo (JP)

( * ) Notice: Subject to any disclaimer, the term of this patent is extended or adjusted under 35 U.S.C. 154(b) by 642 days.

(21) Appl. No.: 10/369,695

(22) Filed: Feb. 21, 2003

(65) Prior Publication Data

US 2003/0159947 A1 Aug. 28, 2003

(30) Foreign Application Priority Data

Feb. 22, 2002 (JP) ............... 2002-046116

(51) Int. Cl.
*G01N 33/00* (2006.01)
*G01N 27/08* (2006.01)
*G01N 27/10* (2006.01)

(52) U.S. Cl. .............. 436/108; 422/82.02; 436/52; 436/113; 436/149; 436/150; 436/151; 436/155

(58) Field of Classification Search .............. 422/68.1, 422/81, 82.01–82.02; 436/43, 52, 108, 113, 436/149–151, 155, 183
See application file for complete search history.

(56) References Cited

U.S. PATENT DOCUMENTS 5,399,325 A * 3/1995 von Harpe et al. ........ 423/235

5,882,937 A * 3/1999 Sauer et al. ............ 436/113
6,114,176 A 9/2000 Edgson et al.
2005/0106650 A1 * 5/2005 Godec ..................... 435/12

FOREIGN PATENT DOCUMENTS

| DE | 39 00 119 | 8/1990 |
| EP | 0 614 081 | 9/1994 |
| JP | 58-163866 | 10/1983 |
| JP | 59-160746 | 9/1984 |
| JP | 6-184085 | 7/1994 |
| JP | 2000-338099 | 12/2000 |
| JP | 2001-518047 | 10/2001 |
| JP | 2002-516169 | 6/2002 |
| NL | 8300782 | 10/1984 |
| WO | WO 98/42623 | 10/1998 |
| WO | WO 99/61136 | 12/1999 |

OTHER PUBLICATIONS

Taylor, D. et al, Analytica Chimica Acta 1986, 186, 91-100.*
Kieke, M. L. et al, Journal of Physical Chemistry 1996, 100, 7455-7462.*
Schoppelrel, J. W. et al, Journal of Physical Chemistry 1996, 100, 14343-14351.*

* cited by examiner

*Primary Examiner*—Arlen Soderquist
(74) *Attorney, Agent, or Firm*—Oblon, Spivak, McClelland, Maier & Neustadt, P.C.

(57) ABSTRACT

A method for determining a urea concentration in an aqueous solution containing urea, includes: hydrolyzing the urea in the aqueous solution, measuring an electric conductivity $\chi$ of the aqueous solution, and determining the urea concentration in the aqueous solution from the electric conductivity $\chi$ using a correlation between the urea concentration and an electric conductivity.

10 Claims, 2 Drawing Sheets

METHOD AND APPARATUS FOR DETERMINING UREA CONCENTRATION

BACKGROUND OF THE INVENTION

1. Field of the Invention

This invention relates to a method for determining a urea concentration in an aqueous solution and an apparatus therefor. This invention may be suitably applied to, for example, a method and an apparatus for determining a urea concentration in a condensate processed in a condensate processing facility during a urea production process, and an apparatus that is capable of sending a signal for controlling a destination of the condensate, based on a urea concentration to a controller such as a distributed control system (DCS).

2. Description of the Related Art

In the past, techniques such as colorimetry or application of a nitrogen analyzer have been used to determine a concentration of urea in a solution. After removing dissolved urea, ammonia and carbon dioxide from the condensed water, the condensed water is then recycled to the production process for being reused as water required in the production process. The term "condensate" as used herein refers to condensed water discharged from, for example, a urea production process, which contains, e.g., urea, ammonia and carbon dioxide.

For example, a method for determining a urea concentration in a solution by colorimetry has been disclosed in Japanese Laid-open Patent Publication No. 2000-338099. However, due to a flaw in the colorimetry measurement system, subtle turbidity in a sample may disturb correct determination of the urea concentration using colorimetric determination method.

A second method using a nitrogen analyzer measures the amount of nitrogen by combusting a measuring sample in the presence of a catalyst to convert nitrogen into nitrogen monoxide and determining a nitrogen monoxide concentration. One drawback of this method is that a nitrogen analyzer determines a total nitrogen content in the measuring sample, and cannot selectively determine a urea concentration.

Additionally, in both methods, a calibration curve must be created using a dedicated standard solution before measurement and precise dilution. The creation of the calibration curve requires additional work, and may introduce inaccuracies from the operator's calculations. Moreover, it is difficult to quickly determine only a urea concentration in a solution in which urea and ammonia coexist using the above-described techniques.

Japanese Laid-open Patent Publication S59-160746 (1984) describes that a urea concentration in a solution is determined utilizing an electric conductivity. This method utilizes an enzyme, particularly for determining a urea level in blood. According to this method, urea concentration is determined by immobilizing an enzyme capable of decomposing urea into ammonia and carbon dioxide on a membrane, passing a solution containing urea through the membrane, absorbing ammonia decomposed by the enzyme into an absorbent solution and measuring an electric conductivity of the absorbent solution. However, a decomposition state (a decomposition rate) for urea may vary depending on enzyme activity and may be susceptible to temperature changes at the place where the membrane is fixed. Much maintenance effort is, therefore, required for keeping higher measuring precision. Furthermore, due to membrane deterioration over time, the membrane must be replaced, leading to troublesome maintenance. In addition, this measuring procedure requires a separate buffer solution during measurement, leading to an increase in running costs.

Japanese Laid-open Patent Publication H06-184085 (1994) describes a process for controlling a urea production plant using electric conductivity. This process involves measuring an ammonia concentration in an ammonium carbamate using an electric conductivity and controlling the total amount of water supplied to a urea synthesizing tube, but does not involve determination of a urea concentration. As a further problem, it requires precise dilution and expensive reagents and catalyst, leading to a higher cost for maintenance.

For example, a processed condensate from a condensate processing facility in the urea production process contains urea. Thus, when the condensate is effectively utilized for, e.g., boiler feed water, quality determination for the fed condensate is time consuming. It is therefore difficult to quickly determine whether the condensate meets the conditions for boiler feed water. An elevated urea concentration in the condensate may result in hydrolysis of urea into ammonia and carbon dioxide in a boiler, which may then cause internal corrosion of the boiler, leading to difficulty in effective utilization of the condensate and thus to difficulty in the conservation of energy and resources.

In light of the above-described difficulties, an objective of the present invention is to provide a method and an apparatus whereby urea concentration in a solution containing urea may be quickly and accurately determined using a convenient and inexpensive apparatus, without dilution of a solution to be measured and without creating a calibration curve upon measurement. Another objective of this invention is to provide a method and an apparatus for determining a urea concentration, whereby on-line water quality management of a urea-containing solution may be continuously conducted.

SUMMARY OF THE INVENTION

After intense investigation, the inventors have found that the above-identified problems may be solved by heating an aqueous solution containing urea under increased pressure, thereby hydrolyzing urea in the solution. The urea concentration is then determined using the electric conductivity of the solution containing hydrolysis products including ammonia, which is proportional to the contents of solutes, such as ammonia. The inventors have also found that when an aqueous solution to be measured contains a substance, such as ammonia, which may change electric conductivity, the above problems may be solved by measuring electric conductivity before and after hydrolysis of urea, respectively, and determining a urea concentration in the solution from the difference between these electric conductivities.

This invention provides a method for determining a urea concentration in an aqueous solution including hydrolyzing the urea in the aqueous solution, measuring an electric conductivity $\chi$ of the resulting aqueous solution, and determining the urea concentration in the aqueous solution from the electric conductivity $\chi$ using a correlation between a urea concentration and an electric conductivity. In this method, it is preferable to continuously conduct sampling of the aqueous solution, hydrolysis of urea in the aqueous solution, and measurement of the electric conductivity $\chi$ to continuously determine a urea concentration in the aqueous solution.

This invention also provides a method for determining a urea concentration in an aqueous solution containing urea, including measuring an electric conductivity $\chi'_1$ in the aqueous solution, then hydrolyzing urea in the aqueous solution, then measuring an electric conductivity $\chi$ in the resulting aqueous solution, and determining a urea concentration in the aqueous solution from the difference between the electric conductivities $\chi$ and $\chi'$ using a correlation between a urea concentration and an electric conductivity. In this method, it is preferable to continuously conduct sampling of the aqueous solution, measurement of the electric conductivity $\chi'$, hydrolysis of urea in the aqueous solution and measurement of the electric conductivity $\chi$ for continuously determining a urea concentration in the aqueous solution.

Hydrolysis may be conducted by pressurizing and heating the aqueous solution. It is preferable that the above heating process is conducted at an aqueous solution temperature of 170° C. to 300° C., with the pressure set in a range that does not cause the solution to boil.

This invention also provides an apparatus for determining urea concentration in an aqueous solution containing urea, including pressurizing means for pressurizing the aqueous solution, heating means for heating the pressurized aqueous solution, a reaction vessel for hydrolysis of urea in the aqueous solution, and conductivity measuring means for measuring an electric conductivity of a aqueous solution discharged from the reaction vessel. This invention also provides an apparatus for determining a urea concentration in an aqueous solution containing urea, including, first conductivity measuring means for measuring a first electric conductivity of the aqueous solution, pressurizing means for pressurizing the aqueous solution whose electric conductivity has been measured by the first measuring means, heating means for heating the pressurized aqueous solution, a reaction vessel for hydrolysis of urea in the aqueous solution, and second conductivity-measuring means for measuring a second electric conductivity of a discharged aqueous solution from the reaction vessel.

The above-described devices preferably also include signal-output means for outputting a signal corresponding to the measured electric conductivity.

DETAILED DESCRIPTION OF THE INVENTION

Figure 1:
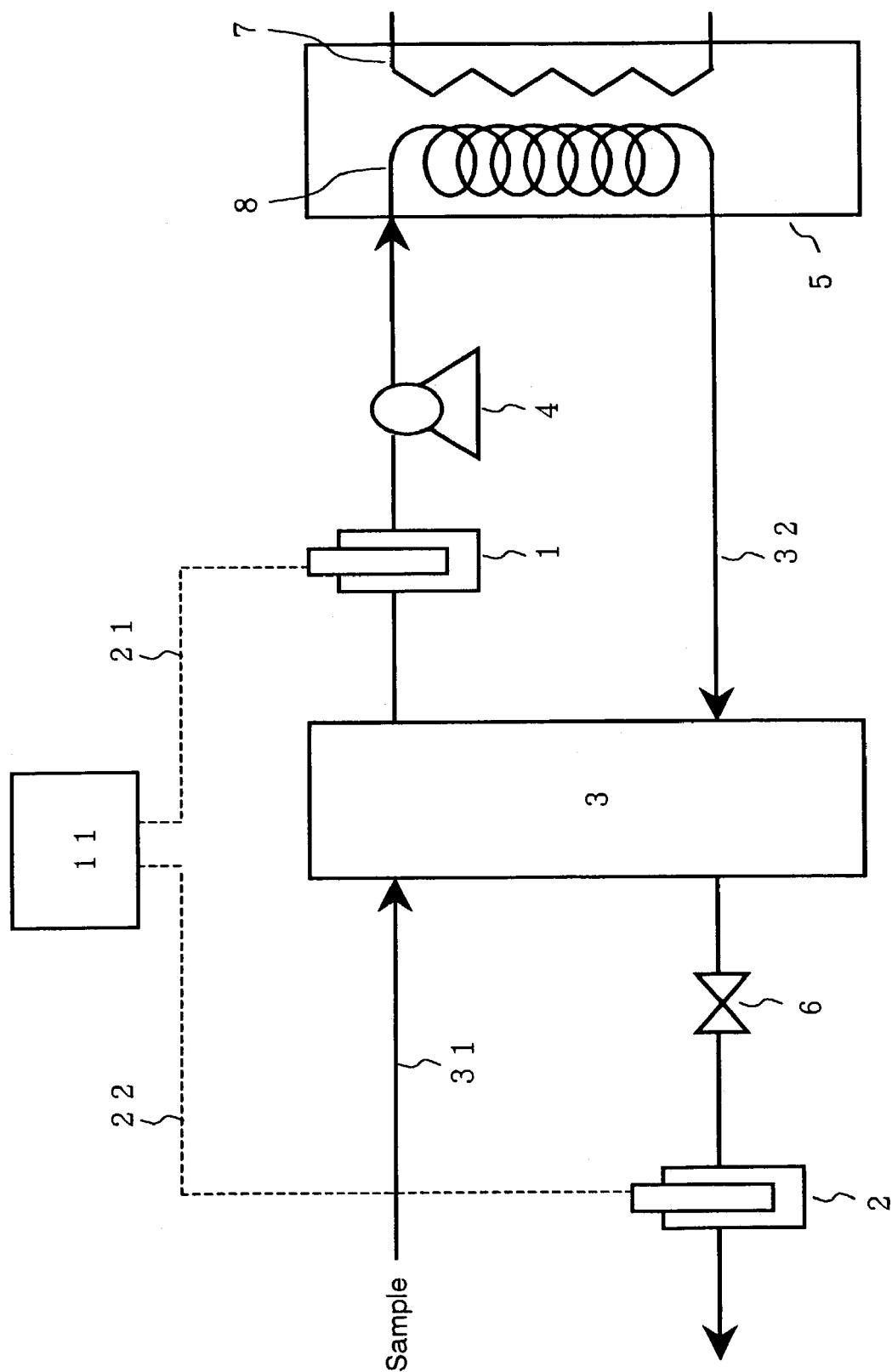
FIG. 1 schematically shows an overall configuration of an embodiment of an apparatus according to this invention.

The terms "%" and "ppm" as used below are based on a weight, unless otherwise indicated.

Urea is hydrolyzed by heating in the presence of water into ammonia and carbon dioxide. A hydrolysis rate depends on a temperature. Specifically, the higher temperature is, the larger the hydrolysis rate is.

A hydrolysis time is a period from initiation of hydrolysis (by heating an aqueous urea solution) to termination of hydrolysis after cooling, but may be practically considered to be a residence time in a reaction vessel when a residence time of the aqueous urea solution in a line 32 is adequately shorter than that in the reaction vessel.

In this invention, urea in an aqueous urea containing solution to be measured (hereinafter, referred to as "sample solution") is hydrolyzed into ammonia and carbon dioxide in a solution state. Although 100% hydrolysis of urea is preferable in light of measuring accuracy, the hydrolysis rate depends on temperature, as described above. An increase in temperature alone may cause the solution to boil, leading to insufficient water for hydrolysis. Thus, it often becomes difficult to obtain ammonia produced by the hydrolysis of urea. It is therefore preferable that a sample solution is pressurized such that the sample solution is not boiled even at a higher temperature, to improve measuring accuracy.

The amount of time required for hydrolysis depends on temperature and pressure. The time for hydrolysis significantly influences measurement time in this invention, and temperature and pressure in hydrolysis may be determined according to a desired measurement time.

A solution to be measured in this invention may be, for example, an aqueous solution in which urea, ammonia, and carbon dioxide are dissolved in water. It is preferable, in light of measuring accuracy, that the amounts of components other than urea, ammonia, and carbon dioxide are negligible in the aqueous solution. An example of such an aqueous solution is condensed water discharged from a urea production process, known as a condensate. The present invention is suitable for determination of a urea concentration in the condensate.

A reaction vessel for hydrolysis may be appropriately designed, taking into account a residence time, reaction conditions (i.e., temperature and pressure), and corrosion resistance. A suitable material for a reaction vessel or pipeline may be, for example, stainless steel.

Process for Determining the Conditions for Urea Hydrolysis

The following examples are useful for describing a process for determining the conditions for hydrolysis of urea in a sample solution according to the present invention. Basically, a maximum urea concentration in an envisioned sample solution is estimated; conditions are determined so that urea in a solution having the maximum urea concentration is hydrolyzed, preferably to a level below a measuring limit in colorimetry, using PDBA (p-dimethyl aminobenzaldehyde) (hereinafter, referred to as "PDBA colorimetry"); and a time required for the hydrolysis is based on a desired urea measuring time as much as possible. Parameters include temperature, pressure, and duration of hydrolysis.

Urea is preferably hydrolyzed to a level below a measuring limit in PDBA colorimetry as described above, to guarantee that a measurable urea concentration range (measuring range) by the measuring method according to this invention covers the envisioned maximum urea concentration, and to guarantee adequate measuring accuracy in the measuring method of this invention. When reduction of measuring time is the highest priority, at a cost of other elements, the hydrolysis does not have to be conducted to a level below the measuring limit in PDBA colorimetry. In general, the measuring limit in PDBA colorimetry is 1 ppm or less.

The hydrolysis conditions may be determined using the apparatus illustrated in FIG. 1. The apparatus in FIG. 1 represents a non-limiting example of an apparatus for measuring urea concentration according to this invention, but one of ordinary skill in the art would be able to determine equivalent devices without departing from the scope of the present invention.

First, an aqueous urea solution at a known concentration is prepared. The aqueous urea solution may be prepared by, for example, dissolving 99.4% pure industrial urea (available from Mitsui Chemicals, Inc.) in purified water. Purified water is preferably water with an electric conductivity of 1.0 µS/cm or less treated with, e.g., an ion-exchange resin.

The aqueous urea solution fed from a line 31 is pressurized to a predetermined pressure by pressurizing means 4. The pressurized aqueous urea solution is introduced to a reaction vessel 8, where the solution is heated by heating means 7. For example, a reactor 5 equipped with heating means 7 may be used.

The aqueous urea solution discharged from the reaction vessel is introduced to cooling means 3, where it is cooled to an ambient temperature. After releasing a pressure by pressure retaining means 6, the solution is discharged from the apparatus. A urea concentration in the discharged aqueous urea solution is then determined by PDBA colorimetry.

The operation conditions in the pressurizing means, the heating means, and the pressure-retaining means are adjusted to alter the settings for temperature, pressure, and the desired time. This process is repeated to determine urea concentrations in a urea solution after hydrolysis for multiple combinations of hydrolysis conditions. From the results thus obtained, the hydrolysis conditions under which urea is reduced to a level below the measuring limit in PDBA colorimetry are determined. Hydrolysis conditions for urea suitable to a desired measuring time are then determined. In view of maximizing measuring accuracy and a measuring range, it is preferable that conditions under which a urea level is below a measuring limit in PDBA colorimetry are determined, but depending on required measuring accuracy or measuring range, not the conditions under which a urea level is below a measuring limit in PDBA colorimetry, but those under which a urea concentration according to PDBA colorimetry is below a given level can be determined.

A hydrolysis temperature is preferably 170° C. or higher in light of hydrolysis rate and reduction in a hydrolysis time, and preferably 300° C. or lower. At more than 300° C., hydrolysis rate is not significantly improved. Reaction pressure is preferably in the range in which a sample solution is not boiled. For example, 1 to 10 MPaG (Gauge) is preferable.

Correlation between Urea Concentration and Electric Conductivity

Figure 2:
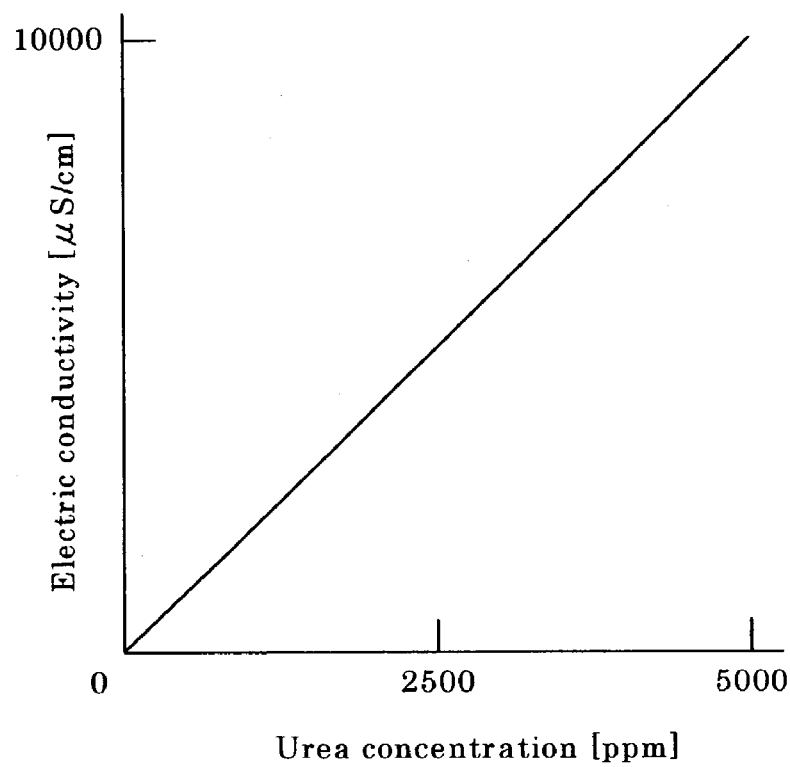
FIG. 2 is a graph showing correlation between a urea concentration and an electric conductivity at 25° C.

This invention also relates to a measuring method utilizing correlation between a variation in an electric conductivity before and after hydrolyzing urea in a solution and an amount of hydrolysis products. FIG. 2 shows a correlation between a urea concentration and an electric conductivity. This correlation is obtained as follows: preparing a plurality of standard aqueous urea solutions having different urea concentrations; sufficiently hydrolyzing each standard solution; confirming by PDBA colorimetry that the urea concentration after hydrolysis is below a measuring limit (1 ppm) in PDBA colorimetry; measuring an electric conductivity $\chi$ of each aqueous solution after hydrolysis at 25° C. using a conductivity meter; and graphing a relationship between a urea concentration and an electric conductivity $\chi$ for each standard solution. In constructing the correlation shown in FIG. 2, a solution including 99.4% pure industrial urea (available from Mitsui Chemicals, Inc.) in purified water was used as a standard aqueous urea solution. Influence of the urea per se on electric conductivity is negligible.

The correlation shown in FIG. 2 applies when the measuring temperature of electric conductivity is 25° C., and a calibration curve does not have to be created upon determining a urea concentration. When an actual measuring temperature is not 25° C., correlation at the actual measuring temperature may be determined in advance or, alternatively, temperature dependency of an electric conductivity $\chi$ may be determined in advance so that a urea concentration can be determined using the correlation in FIG. 2 after temperature correction of an electric conductivity within a desired temperature range. In this invention, a urea concentration may be determined by either of the following two methods using the above correlation.

Method 1:
Urea in a sample solution to be measured is hydrolyzed; then an electric conductivity $\chi$ of the hydrolyzed solution is measured; and a urea concentration in the sample solution is then determined from the electric conductivity $\chi$ using the above urea concentration-electric conductivity correlation.

Method 2:
An electric conductivity $\chi'$ of a sample solution is measured; then urea in the sample solution is hydrolyzed; then an electric conductivity $\chi$ of the hydrolyzed solution is measured; and a urea concentration in the sample solution is then determined from a difference $(\chi-\chi')$ between the electric conductivities $\chi$ and $\chi'$ using the above urea concentration-electric conductivity correlation.

Method 1 is best used when the presence of substances influencing electric conductivity other than urea in a urea-containing sample solution is negligible, or when the purpose of the measurement is to track concentration variation rather than accurate determination of an absolute urea concentration value.

Method 2 is best used to determine a urea concentration when a sample solution contains substances influencing an electric conductivity, such as ammonia or others. When correlation between ammonia concentration and electric conductivity is known, a sample solution containing urea and ammonia, and the presence of substances influencing an electric conductivity other than these is negligible, Method 2 may be used to determine a urea concentration from an electric conductivity difference $(\chi-\chi')$ and the above urea concentration-electric conductivity correlation while determining an ammonia concentration in the sample solution from the electric conductivity $\chi'$ and the ammonia concentration-electric conductivity correlation.

Figure 3:
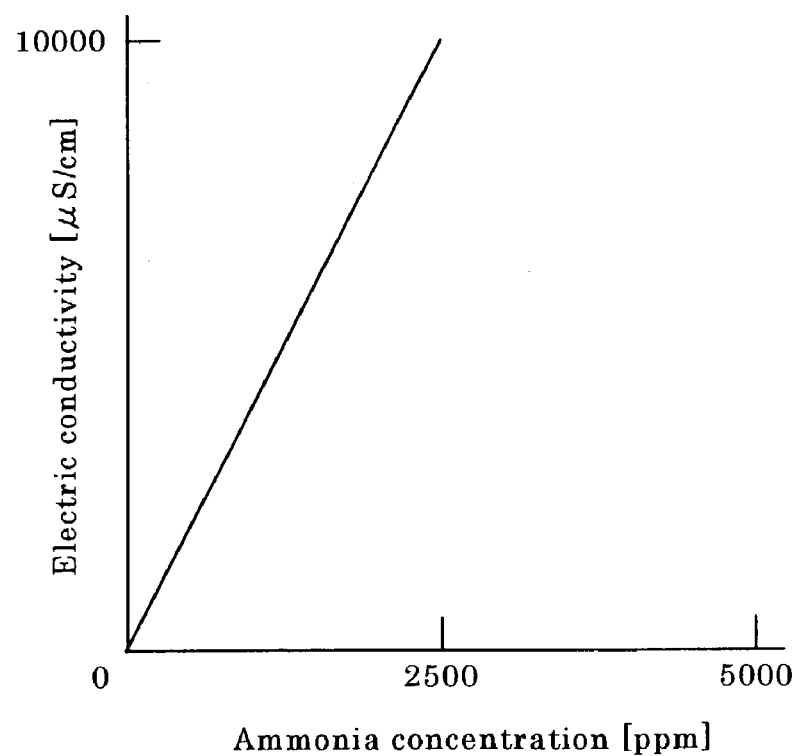
FIG. 3 is a graph showing correlation between an ammonia concentration and an electric conductivity at 25° C.

FIG. 3 shows a correlation between an ammonia concentration and electric conductivity. The correlation is obtained as follows: measuring electric conductivities at 25° C. using a conductivity meter for a plurality of standard aqueous ammonia solutions having different ammonia concentrations, and graphing a relationship between ammonia concentration and electric conductivity for each standard aqueous ammonia solution. In constructing the correlation shown in FIG. 3, a solution 25% aqueous ammonia in purified water was used as a standard aqueous ammonia solution.

The correlation shown in FIG. 3 also applies when the measuring temperature of electric conductivity is 25° C., and a calibration curve does not have to be created upon practical determination. When an actual measuring temperature is not 25° C., ammonia concentration-electric conductivity correlation at the actual measuring temperature may be determined in advance or, alternatively, temperature dependency of an electric conductivity of an aqueous ammonia solution may be determined in advance so that an ammonia concentration may be determined using the correlation in FIG. 3 after temperature correction of an electric conductivity within a desired temperature range.

In any case, when a sample solution contains substances that may alter an electric conductivity of a sample solution before and after hydrolysis other than urea, a measuring accuracy for a urea concentration may be degraded. Thus, this invention is particularly useful when the presence of such substances is negligible.

As described earlier, FIG. 1 shows a typical configuration of an apparatus for conducting a method of this invention. The apparatus includes cooling means 3 for cooling a sample solution; pressurizing means 4 for pressurizing a sample solution; a reactor 5 comprising heating means 7 for hydrolyzing a sample solution and a reaction vessel 8; cooling means 3 for cooling the hydrolyzed sample solution; pressure-retaining means 6 such as an autonomous valve for retaining a pressurized state; conductivity-measuring meters/apparatus (hereinafter, referred to as "sensor") 1 and 2 such as a conductivity meter for measuring an electric conductivity; and lines (piping). For sensors 1 and 2, sensors having a measuring range suitable for a urea concentration in a sample solution are selected. For example, a conductivity meter may be used to measure a urea concentration in the range of 0 to 5000 ppm according to this invention.

In FIG. 1, single cooling means 3 is used upstream of the sensor 1 and the sensor 2, but separate cooling means may also be used. When a sample solution temperature is lower than a measuring temperature range, the cooling means 3 upstream of the sensor 1 may be replaced with warming/heating means. When the temperature of a solution to be measured for its electric conductivity is within a measuring temperature range for the sensor, the cooling means or the warming/heating means upstream of the sensor is unnecessary.

First, a sample solution is taken via a line 31 from a line in which a solution to be measured for its urea concentration flows or a tank storing the solution (not shown) in, for example, a condensate processing facility, and the sample solution is introduced into the cooling means 3 to be cooled to a measuring temperature range of the sensor 1, for example, to 20° C. to 60° C. When a sample solution temperature is lower than a measuring temperature range of the sensor 1, the cooling means 3 is replaced with warming/heating means to adjust a sample solution temperature within a measuring temperature range of the sensor 1.

The temperature-adjusted sample solution is determined for its electric conductivity by the sensor 1. This measurement gives an electric conductivity corresponding to the total amount of substances such as ammonia that may alter an electric conductivity in the sample solution. The sample solution, after passing through the sensor 1, is pressurized, preferably to 1 to 10 MPaG, by pressurizing means 4, such as a pump, and then fed into the reactor 5, which may be equipped with heating means.

When it is known that no substances capable of altering an electric conductivity are contained in the sample solution or, if present, they are negligible in determining urea concentration, the sensor 1 may be omitted and the sample solution may be directly pressurized by pressurizing means 4, such as a pump, and fed into the reactor 5. This configuration is suitable for an apparatus used in Method 1.

Heating means may include heaters that use electricity or a heating medium such as steam. Pressurizing means 4 is preferably a metering pump because a hydrolysis time can be easily controlled. Cooling means may include coolers that use water or other liquid coolant. Alternatively, an air cooled heat exchanger may be used as the cooling means.

Pressurizing means, heating means, and pressure-retaining means described below are used to realize the hydrolysis conditions determined by the above-mentioned method for determining urea hydrolysis conditions in a reaction vessel 8. Thus, urea in a sample solution is decomposed into ammonia and carbon dioxide (hereinafter, referred to as "hydrolysis products").

The sample solution containing the hydrolysis products is cooled to a measuring temperature range of the sensor 2 by the cooling means 3, its pressure is adjusted to a measuring pressure range of the sensor by pressure-retaining means 6, and then an electric conductivity is determined by the sensor 2. A urea concentration in the sample solution is derived from a difference of electric conductivity values between the sensor 1 and the sensor 2 ($\chi-\chi'$) and the above correlation.

For example, when it is known that a sample solution contains no substances capable of altering electric conductivity and the sensor 1 is omitted, urea concentration in the sample solution may be determined from the electric conductivity from the sensor 2 and the above correlation.

In FIG. 1, as appropriate, a preheater for preheating the sample solution may be disposed between the pressurizing means 4 and the reaction vessel 8. It is not necessary to use a reactor including heating means and a reaction vessel, but a sample solution may be heated by heating means located upstream of the reaction vessel, and then introduced to the reaction vessel and hydrolyzed for a desired residence time.

The sample solution is preferably processed in a closed system to prevent the sample solution from being exposed to the air between sampling the aqueous solution to be a sample solution and the end of determination of an electric conductivity. If the sample solution is exposed to air, substances influencing an electric conductivity in the air might dissolve in the sample solution, thereby altering the electric conductivity of the sample solution, and possibly leading to measurement error.

The apparatus of the present invention is preferably equipped with signal-output means that outputs signals 21 and 22 (i.e., electric signals) corresponding to determined electric conductivity values because the signals may be sent to a control means such as a DCS 11 to be utilized by the control means. It is possible to automatically determine urea concentration, by using such signal-output means together with a control means, e.g. a DCS, to which correlation between a urea concentration and an electric conductivity has been already input as a function. Also, ammonia concentration may be automatically determined, when the control means stores a function which corresponds to correlation between an ammonia concentration and an electric conductivity.

For example, when a condensate is utilized as boiler feed water, the following procedure may be used. Specifically, a sample solution is continuously sampled from a condensate, the sample solution is continuously hydrolyzed, electric conductivity $\chi$ after hydrolysis (and if necessary an electric conductivity $\chi'$ before hydrolysis) are continuously determined, and then electric signals corresponding to the electric conductivities $\chi$ and, as necessary, $\chi'$ are continuously sent to the DCS. The DCS, to which correlation between a urea concentration and an electric conductivity has been already input as a function, reconverts the received electric signal into an electric conductivity value, then converts the electric conductivity into a urea concentration to display and record the urea concentration in the condensate. The DCS may then be controlled to feed the condensate to the boiler when the urea concentration is within a given range, and to stop feeding the condensate to the boiler when the urea concentration is above a given range.

When $\chi'$ is utilized in addition to $\chi$, it is preferable to consider a time delay from passing of the sample solution through the sensor 1 to its arriving at the sensor 2. Specifically, when the time delay is $\Delta t$, an electric conductivity $\chi'(t)$ is determined by the sensor 1 at time t and when the sample solution arrives at the sensor 2 at time (t+$\Delta t$) after hydrolysis, an electric conductivity χ(t+Δt) is determined, it is preferable that χ'(t) is stored in the DCS to calculate a conductivity difference {χ(t+Δt)−χ'(t)}, and that the difference and the above correlation are used to determine urea concentration in the sample solution. When variation in urea concentration in the condensate is insignificant during a measuring time, it may be practically acceptable to determine urea concentration simply from a conductivity difference {χ(t)−χ'(t)}, while neglecting a time delay. A time delay may be calculated from a flow rate of the sample solution flowing in the urea-concentration measuring apparatus and a volume of, for example, a line from the sensor 1 to the sensor 2.

The electric signals 21 and 22 may be a current, e.g., having a range of 4 mA to 20 mA or a voltage, e.g., having a range of 1 V to 5 V. It is convenient and preferable to use sensors with built-in circuit and terminals to condition and connect the electric signals in order to measure an electric conductivity and send the corresponding electric signals to a control means. To send the signals to DCS, a transmitter, an amplifier or an analog-digital/digital-analog converter, commonly used in instrumentation filed, may also be used.

EXAMPLES

This invention will be specifically described with reference to several non-limiting examples. In these examples, this invention is applied to determination of a urea concentration in a processed condensate from a condensate processing facility in a urea production process and to effective utilization of the processed condensate. A processed condensate from a condensate processing facility in a urea production process generally contains ammonia, urea, and carbon dioxide.

Determination of the Urea Hydrolysis Conditions

The urea hydrolysis conditions were determined using the apparatus shown in FIG. 1, as described in the above detailed description of preferred embodiments. Sample solutions were prepared by dissolving 99.4% pure industrial urea (available from Mitsui Chemicals, Inc.) in purified water to give sample solutions containing urea at 30 and 35 ppm.

A urea concentration in a solution after hydrolysis was measured by a colorimeter (spectrophotometer) whose calibration curve had been created according to the instructions for the apparatus. Measurement was conducted by PDBA colorimetry 10 minutes after adding a PDBA color former, using a spectrophotometer available from Hitachi, Ltd. (Brand Name: HITACHI-U1000 Spectrophotometer) with a wavelength of 430 nm and a cell length of 50 mm and using a solution prepared by adding the PDBA color former to purified water as a control.

The measurement results are shown in Table 1. From the measurement results, among the combinations of the conditions where a urea concentration was below a measuring limit in PDBA colorimetry (1 ppm), the combination of a heating temperature: 220° C., a pressure: 2.5 MPaG, and a hydrolysis time: 10 minutes, were selected as the hydrolysis conditions.

TABLE 1

| Run | Heating temp. ° C. | Pressure MPa | Hydrolysis time min | Urea conc. in a sample solution (before hydrolysis) ppm | Urea conc. in a sample solution (after hydrolysis) ppm |
|---|---|---|---|---|---|
| A1-1 | 220 | 2.5 | 2.5 | 30 | 2.3 |
| A1-2 | 220 | 2.5 | 2.5 | 30 | 2.8 |
| A2-1 | 220 | 2.5 | 5.0 | 30 | 2.4 |
| A2-2 | 220 | 2.5 | 5.0 | 30 | 1.4 |
| A3-1 | 220 | 2.5 | 7.5 | 30 | less than 1 |
| A3-2 | 220 | 2.5 | 7.5 | 30 | less than 1 |
| A4-1 | 220 | 2.5 | 10.0 | 30 | less than 1 |
| A4-2 | 220 | 2.5 | 10.0 | 30 | less than 1 |
| B1-1 | 180 | 1.3 | 12.5 | 35 | 2.6 |
| B1-2 | 180 | 1.3 | 12.5 | 35 | less than 1 |
| B2-1 | 180 | 1.3 | 12.5 | 35 | 1.9 |
| B2-2 | 180 | 1.3 | 12.5 | 35 | less than 1 |
| C1-1 | 190 | 1.5 | 7.5 | 35 | 8.4 |
| C1-2 | 190 | 1.5 | 7.5 | 35 | 7.9 |
| C2-1 | 190 | 1.5 | 10.0 | 35 | 9.7 |
| C2-2 | 190 | 1.5 | 10.0 | 35 | 8.6 |
| C3-1 | 190 | 1.5 | 12.5 | 35 | less than 1 |
| C3-2 | 190 | 1.5 | 12.5 | 35 | less than 1 |
| D1-1 | 200 | 1.8 | 12.5 | 35 | less than 1 |
| D1-2 | 200 | 1.8 | 12.5 | 35 | less than 1 |

Example 1

In the apparatus shown in FIG. 1, the sensors 1 and 2 were conductivity meters from HORIBA Inc. (Model: TD-920). The cooling means 3 was a cooler using water. The pressurizing means 4 was a metering pump from Nippon Seimitsu Kagaku Inc. (Model: NR-S-702). The heating means in the reactor 5 was an electric heater, and a coiled stainless tube was placed in the reactor as the reaction vessel 8. All the pipes in the apparatus were made of stainless steel. The pressure-retaining means 6 was a commercially available pressure regulator that may be used for an ammonia-containing solution.

In this apparatus, a part of a solution containing ammonia and urea from a condensate facility in a urea production process was fed through a line 31 into the cooler at a rate of 10 mL/min. The sample solution was cooled to 25° C. and electric conductivity χ' was then determined by the sensor 1. The solution was subsequently introduced into the reactor while being pressurized to 2.5 MPaG by the metering pump. The solution was heated to 220° C. by the electric heater and hydrolyzed with hydrolysis time of 10 minutes. Urea in the solution was hydrolyzed to a level below the measuring limit in PDBA colorimetry. The solution containing the hydrolysis products discharged from the reactor was reintroduced into the cooler to be cooled to 25° C. Pressure was adjusted by the pressure-retaining means to a measuring pressure range of the sensor 2, and then an electric conductivity χ was determined.

Electric conductivities were obtained from the sensor 1 and the sensor 2, and a difference between the electric conductivities from the sensors 1 and 2 was calculated. Then, from the correlations shown in FIGS. 2 and 3, ammonia and urea concentrations in the sample solution were determined.

The ammonia and the urea concentrations were 10 ppm and 12 ppm, respectively. For confirmation, the above solution was measured for its ammonia concentration by the indophenol method and for its urea concentration by PDBA colorimetry.

These confirmation measurement results are shown in Table 2. As seen from Table 2, there is good conformity between the measurement results according to this invention and those for confirmation, indicating that the measuring method and the apparatus according to this invention are effective.

Measurement of an ammonia concentration by an indophenol method was conducted by a spectrophotometer available from Hitachi, Ltd. (Model: HITACHI-U1000) with a measuring wavelength of 640 nm and a cell length of 10 mm, using a blank test solution (prepared by adding phenol-sodium nitroprusside and sodium hypochlorite to purified water) as a control.

Reference Example 1

Electric conductivity $\chi'$ was determined by the sensor 1 as described in Example 1 for an ammonia-containing aqueous solution that contained no substances, other than ammonia, that may influence electric conductivity. As a result, the ammonia concentration was determined to be 10 ppm. For confirmation, the above solution was measured for its ammonia concentration by the indophenol method. These measurement results are shown in Table 2. As seen from Table 2, for an ammonia concentration, there is also good conformity between the measurement results according to this invention and those for confirmation.

Example 2

Measurement was conducted for an aqueous solution containing urea in which substances influencing an electric conductivity other than urea are negligible under the apparatus/measurement conditions described in Example 1. As a result, urea concentration was determined to be 10 ppm. For confirmation, the above solution was measured for its urea concentration by PDBA colorimetry. These measurement results are shown in Table 2. As seen from Table 2, there is good conformity between the measurement results according to this invention and those for confirmation, indicating that the measuring method and the apparatus according to this invention are effective.

Example 3

For utilizing a mixture of the processed condensate from the condensate processing facility in the urea production process and a processed condensate from another production process as a feed water for an industrial boiler (100 K scale), a test was conducted where a urea concentration in the condensate from the urea production process was measured using the apparatus of this invention; the measured value was sent to the DCS 11 via signals 21 and 22; and the measured value was compared with a preset value in the DCS 11 to judge whether a mixture with the processed condensate from the other production process was suitable as a boiler feed water to automatically change a flow channel of the condensate from the urea production process depending on the judge results. The sensors 1 and 2 included signal output means (not shown) outputting electric signals 21 and 22, respectively, corresponding to the measured electric conductivities, which were connected to the DCS via an instrument wiring.

When a urea concentration in the condensate from the urea production process is less than the preset value, the condensate from the urea production process is fed to a mixing line, in which it is mixed with the condensate from the other production process. Otherwise, a flow channel is changed for stopping feeding to the mixing line. The preset value was 5 ppm.

As shown in Table 2, when a urea concentration in the condensate from the urea production process was 2.3 ppm, the condensate was fed to the mixing line; when the urea concentration was 8.5 ppm, the flow channel was automatically changed to stop feeding of the condensate to the mixing line; and then, when the urea concentration was 3.3 ppm, the flow channel was automatically changed to feed the condensate to the mixing line.

Thus, it has been confirmed that the apparatus of this invention and the DCS may conduct measurement for a urea solution in a condensate and automatically judge whether the results are acceptable for utilizing the condensate in a desired process to automatically change a destination of the condensate.

TABLE 2

|  | Exam. 1 | Ref. Exam. 1 | Exam. 2 | Exam. 3 | | |
|---|---|---|---|---|---|---|
| Ammonia conc. determined from the correlation in FIG. 3 (ppm) | 10 | 10 | — | — | — | — |
| Urea conc. determined from the correlation in FIG. 2 (ppm) | 12 | — | 10 | 2.3 | 8.5 | 3.3 |
| Ammonia conc. by the indophenol method (ppm) | 9.6 | 9.2 | — | — | — | — |
| Urea conc. by the PDBA method (ppm) | 12.2 | — | 10.4 | — | — | — |
| Feeding to the mixing line |  |  |  | Feed | Do Not feed | Feed |

As described above, this invention provides a method and an apparatus for determining a urea concentration, which allow a urea concentration in a urea-containing solution to be accurately and quickly determined using a simple apparatus configuration without diluting a sample solution upon measurement, and to allow on-line water quality management of the urea-containing solution to be continuously conducted.

Numerous modifications and variations of the present invention are possible in light of the above teachings. It is therefore to be understood that within the scope of the appended claims, the invention may be practiced otherwise than as specifically described herein.

What is claimed is:

1. A method for determining an original urea concentration in an aqueous solution containing urea, comprising:
   hydrolyzing the urea in the aqueous solution to a level of 1 ppm or less at a temperature between about 170° C. to about 300° C. and at a pressure at which the aqueous solution is not boiled;
   measuring an electric conductivity $\chi$ of the aqueous solution after hydrolysis; and determining the original urea concentration in the aqueous solution from the electric conductivity $\chi$ using a correlation between the urea concentration and the electric conductivity.

2. The method according to claim 1, wherein hydrolysis of urea in the aqueous solution, and measurement of the electric conductivity are continuously conducted.

3. The method according to claim 2, wherein the amount of substances influencing the electrical conductivity of said aqueous solution other than urea is negligible.

4. The method according to claim 3, wherein the correlation between the urea concentration and the electric conductivity is linear.

5. The method according to claim 1, wherein the amount of substances influencing the electrical conductivity of said aqueous solution other than urea is negligible.

6. The method according to claim 5, wherein the correlation between the urea concentration and the electric conductivity is linear.

7. The method according to claim 1, wherein the correlation between the urea concentration and the electric conductivity is linear.

8. A method for determining an original urea concentration in an aqueous solution containing urea and one or more substances influencing the electric conductivity of said solution, comprising:

measuring an electric conductivity $\chi'$ in the aqueous solution;

hydrolyzing the urea in the aqueous solution to a level of 1 ppm or less at a temperature between about 170° C. to about 300° C. and at a pressure at which the aqueous solution is not boiled;

measuring an electric conductivity $\chi$ in the hydrolyzed aqueous solution; and determining the original urea concentration in the aqueous solution from a difference between the electric conductivities $\chi$ and $\chi'$ using a correlation between the urea concentration and the electric conductivity.

9. The method according to claim 8, wherein measurement of the electric conductivity $\chi'$, hydrolysis of urea in the aqueous solution, and measurement of the electric conductivity $\chi$ are continuously conducted.

10. The method according to claim 8, wherein the correlation between the urea concentration and the electric conductivity is linear.

* * * * *